United States Patent [19]

Ceprini et al.

[11] 4,231,949
[45] Nov. 4, 1980

[54] PROCESS FOR PREPARING ORGANOTIN ESTERS

[75] Inventors: Mario Q. Ceprini, Cedarhurst, N.Y.; John D. Collins, Albrighton, England; Samuel Hoch, Brooklyn, N.Y.; Donald A. Wood, Warley, England

[73] Assignee: Albright & Wilson Limited, Warley, England

[21] Appl. No.: 928,795

[22] Filed: Jul. 28, 1978

[51] Int. Cl.$^2$ .............................................. C07F 7/22
[52] U.S. Cl. .................................................. 260/429.7
[58] Field of Search ...................................... 260/429.7

[56] References Cited

U.S. PATENT DOCUMENTS

| | | | |
|---|---|---|---|
| 2,648,650 | 8/1953 | Weinberg et al. | 260/429.7 |
| 2,832,750 | 4/1958 | Weinberg et al. | 260/429.7 |
| 3,115,509 | 12/1963 | Mack | 260/429.7 |
| 3,213,120 | 10/1965 | Besso | 260/429.7 |
| 3,244,737 | 4/1966 | Horan et al. | 260/429.7 |
| 3,433,763 | 3/1969 | Suzuki et al. | 260/429.7 X |
| 3,539,636 | 11/1970 | Dorfelt et al. | 260/429.7 X |
| 3,574,693 | 4/1971 | Fuchsman et al. | 260/429.7 |
| 3,637,777 | 1/1972 | Hoch | 260/429.7 |
| 3,642,846 | 2/1972 | Hoch | 260/429.7 |
| 3,651,107 | 3/1972 | Stanback et al. | 260/429.7 |
| 3,658,860 | 4/1972 | Wirth et al. | 260/429.7 |
| 3,703,588 | 11/1972 | Saito et al. | 260/429.7 |
| 3,920,712 | 11/1975 | Spivack | 260/429.7 |

Primary Examiner—Helen M. S. Sneed
Attorney, Agent, or Firm—Frishauf, Holtz, Goodman & Woodward

[57] ABSTRACT

Organotin esters from acid esters of di or poly carboxylic acids are made by adding a base to a mixture of an organotin halide and the acid ester in the presence of water, and reacting to form the organotin ester, the amount of base and acid ester being to provide 0.9–1.3 equivalents and at least 0.9 equivalents respectively per g. atom of halogen in the organotin halide, and the conditions being such as not to cause substantial hydrolysis.

15 Claims, No Drawings

PROCESS FOR PREPARING ORGANOTIN ESTERS

This invention relates to a process for preparing organotin compounds, in particular organotin carboxylate esters.

Such esters, as exemplified by dibutyltin bis monoalkyl maleates, are usually prepared by reacting the corresponding hydroxide or oxide, e.g. dibutyl tin oxide with a mono ester of a dicarboxylic acid, made by reacting one mole of the dicarboxylic acid anhydride with one mole of alcohol. The organotin oxide or hydroxide is itself made by hydrolysis of the corresponding chloride, e.g. dibutyl tin dichloride with aqueous base, e.g. sodium hydroxide solution. The recovery of the oxide, e.g. dibutyltin oxide at the end of the hydrolysis is troublesome, as the oxide, which is insoluble, is difficult to filter and hence difficult to wash to remove byproduct sodium chloride, any excess of base and water. The oxide also needs to be dried. The presence of water or base in the subsequent reaction with the mono ester of the carboxylic acid can cause hydrolysis of the ester and/or anhydride and/or the desired reaction product.

We have now found a process for preparing the esters directly from the organotin halide without the need for conversion of the halide into oxide.

The present invention provides a process for preparing organotin esters of carboxylic acids, which comprises adding a base, preferably an aqueous solution of alkali metal hydroxide, to an agitated mixture of an organotin halide of formula $(R')_a SnX_{4-a}$ wherein a is an integer of 1 or 2, X is a chlorine, bromine, or iodine atom, each of $R'$ is an organic group e.g. an organic hydrocarbyl group of 1-20 carbon atoms such as an alkyl group of 1-20 carbon atoms, an alkenyl group of 2-18 carbon atoms, a cycloalkyl group, an aryl group, or an aralkyl group, and a carboxyl compound containing at least one carboxylic acid group and at least one carboxylic ester group of formula $(R^2YOC)_m R^3 (COOH)_n$ wherein m and n are each an integer of 1 to 3, $R^3$ is a single bond or an (m+n)-valent organic group e.g. an organic hydrocarbyl group of 1-20 carbon atoms which may optionally have at least one hydroxyl substituent, e.g. a group derived from a saturated or unsaturated aliphatic hydrocarbon of 1-18 carbon atoms, a hydroxy alkane of 2-18 carbon atoms, a cyclo aliphatic hydrocarbon of 4-15 carbon atoms e.g. 5-7 carbon atoms or an aromatic compound, e.g. of 6-19 carbon atoms, and Y is an oxygen or sulphur atom, and $R^2$ is as defined for $R'$, the addition being carried out in the presence of water and producing a second mixture which is reacted to form an organotin ester with at least one $OOCR^3COYR^2$ group attached to a tin atom and preferably two such groups, the amount of said base being to provide 0.9-1.3, e.g. 1.02-1.25 equivalents per g. atom of halogen bonded to tin in the organotin halide, and the amount of said carboxyl compound being sufficient to replace at least 90% of the halogen atoms in the organotin halide. When the carboxyl compound is a mono ester mono acid of a dicarboxylic acid of formula $R^3 (COOH)_2$, the organotin ester is substantially of formula $(R')_a Sn (OOC R^3 COYR^2)_b$ wherein a+b=4, and b is an integer of 2 or 3.

In the above compounds the organic groups represented by $R'$, $R^2$ and $R^3$ are stable under the conditions of the reaction i.e. do not contain reactive groups.

In the above compounds $R'$ may be an alkyl group of 1-18 carbon atoms, e.g. 1-12 carbon atoms, and especially 1-8 carbon atoms, such as methyl, ethyl, propyl, isopropyl, n-butyl, hexyl, n-octyl, iso octyl, 2-ethyl hexyl, decyl, lauryl, cetyl and stearyl, or an alkenyl group of 2-18 carbon atoms, e.g. 2-6 carbon atoms, such as vinyl, allyl, and propenyl, a cycloalkyl group, e.g. of 5-7 carbon atoms, such as cyclohexyl or cyclopentyl, an aryl group (and preferably an aromatic hydrocarbyl group), e.g. of 6-19 preferably 6-12 carbon atoms such as phenyl, tolyl, xylyl and naphthyl or an aralkyl group (preferably an aralkyl hydrocarbyl group) e.g. of 7-19 carbon atoms such as benzyl, β-phenyl-ethyl or benzhydryl. $R^2$ is selected from the same group as $R'$, and may also specifically be an alkoxy-or alkylthio-alkyl group each of 2-18 carbon atoms, e.g. 2-10 carbon atoms especially those with 1-6 carbon atoms in the alkoxy (or alkylthio) and alkyl groups such as the butoxethyl or butyl thioethyl groups. Alternatively $R^2$ may be an alkan-on-yl group such as a propan-2-on-1-yl group. Most preferably, $R'$ is an alkyl group of 1-10 in particular 4-10 carbon atoms, e.g. methyl, n butyl or octyl, or a cyclohexyl or phenyl group. Most preferably $R^2$ is an alkyl group of 1-20 carbon atoms, e.g. 4-18 e.g. 6-10 or 3-10 especially 4-8 carbon atoms or a cyclohexyl group. It is not essential that all the $R'$ groups in the organotin starting material are the same, so that for example, mixed organotin compounds may be used, e.g. butyloctyltin compounds. Similarly, different $R^2$ groups may be used, as for example when $R^2OH$ represents an "OXO" alcohol of, e.g. 8 or 12-16 carbon atoms. Also different X groups may be present in the same molecule.

While in the carboxyl compound of formula $(R^2YOC)_m R^3 (COOH)_n$ m and n are each 1-3, it is preferred that the sum is 2-4 with n 1 or 2 and m 1-3; particularly preferred values of m and n are 1 each.

When the carboxyl ester/acid compound is based on a dicarboxylic acid, (m and n are each 1) $R^3$ may be an alkylene group of 1-18 carbon atoms, preferably 2-10 carbon atoms, such as methylene, ethylene, 1,4 butylene, 1,8 octylene, or an alkenylene group of 2-18 carbon atoms, preferably 2-10 carbon atoms such as —CH=CH—, 1,2-prop-2,3-enylene, (as in itaconic acid) 1,2 prop-1,2-enylene (as in malic acid), or a 1,2-bis hydroxylethylene 1,2 groups (as in tartaric acid), a cycloalkylene group, e.g. of 5-7 carbon atoms such as 1,4-cyclohexylene, an arylene group (preferably a divalent aromatic hydrocarbyl group), e.g. of 6-19 carbon atoms, especially 6-12 carbon atoms, such as phenylene (especially 1,2-naphthylene). Most preferably $R^3$ is a group of formula —CH=CH—, in the cis form (based on maleic acid) or trans form (as in fumaric acid), or an ethylene group. $R^3$ may also be an organic group with 2 or more fused rings, especially bridged rings such as the groups attached to an anhydride group obtained by reacting maleic anhydride with conjugated dienes such as cyclopentadiene and halogenated derivatives thereof, or aliphatic conjugated dienes e.g. to make the acid $R^3 (COOH)_2$ an alkenyl succinic acid. $R^3$ may also be a single bond as in oxalic acid.

When the carboxyl compound is based on an acid with (m+n) carboxyl groups in which the total of m and n is an integer of 3-6, $R^3$ may be an (m+n) valent group based on an alkane of 1-18 carbon atoms, preferably 2-10 carbon atoms, such as propane (as in tricarballylic acid), or a hydroxy substituted derivative of such an alkane, such as propane (as in citric acid), or an alkene of 2–18 carbon atoms, e.g. 2–10 carbon atoms or a cycloalkane, e.g. of 5–7 carbon atoms, or an aromatic compound (e.g. an aromatic hydrocarbon) of 6–19 carbon atoms, especially 6–13 carbon atoms such as benzene (as in mellitic, pyromellitic, benzene-1,2,4,5-tetracarboxylic acid and trimellitic acids). Again bridged polycyclic groups, the nuclei from maleic anhydride/conjugated diene condensation products, may represent $R^3$.

Preferably the carboxylic acid $R^3(COOH)_{m+n}$ is one with a first acid dissociation constant such that its $pK_a$ is not more than 3.2 e.g. 1–3.2, preferably 1–2.5 and especially 1–2 such as 1.5–2. Such acids are to be found among di and tri carboxylic acids, in which $R^3$ is an aliphatic hydrocarbyl group of 1–3 carbon atoms, optionally substituted with 1–3 hydroxyl groups, as in maleic, dihydroxymalic, hydroxytartaric, malonic, fumaric, lactic, tartaric, or an aromatic hydrocarbyl group of 6–8 carbon atoms as in phthalic acid, or in which $R^3$ is a single bond as in oxalic acid.

The reaction is carried out in the presence of base, which is preferably water soluble. It may be inorganic as in the hydroxides, carbonates or bicarbonates of ammonia, alkali metals such as sodium or potassium, alkaline earth metals such as calcium e.g. as CaO or may be a quaternary organic hydroxide, carbonate or bicarbonate, e.g. a tetraalkyl ammonium compound in which each alkyl has 1–8 carbon atoms in each alkyl group such as tetramethyl, tetraethyl—, tetra butyl— or tetraoctyl ammonium. Preferably the base is water soluble and a hydroxide carbonate or bicarbonate of an alkali metal group and especially the amount of base is 90–130%, and preferably 95–125% the amount needed to neutralize the number of moles of hydrogen halide produced in the reaction.

The molar proportion of carboxyl compound to organotin starting materials depends on the number of halogen atoms in the organotin halide and the number of free carboxylic acid groups on the carboxyl compound and desired in the product, but is usually such that for each halogen in the organotin there is 0.9–1.3, preferably 0.98–1.2 (especially at least one) acid equivalent of carboxyl compound per halogen atom. Thus when, as in preferred, a monoester of a dicarboxylic acid is reacted with the organotin halide, there is preferably 0.98–1.2, e.g. about 1 molecule of carboxyl compound per atom of halogen; thus preferably 1 mole of diorganotin dihalide is reacted with 1.95–2.4 moles, (e.g. about 2 moles) of a monoester of a dicarboxylic acid and 1.9–2.5 equivs. of base e.g. an alkali metal or quaternary ammonium hydroxide. The base usually provides 0.9–1.3 e.g. 1.0–1.3 such as 1.02–1.2 equivalents per equivalent of carboxyl group within the broad confines of the range of amount of base to halogen.

The reaction between the organotin halide, the carboxyl compound and base e.g. hydroxide is carried out by mixing the organotin halide and carboxyl compound in the desired proportions and then to the mixture obtained is added the base with agitation. The organotin halide and carboxyl compound may be dissolved in an inert water immiscible liquid solvent such as an aliphatic or cycloaliphatic hydrocarbon of 5–12 carbon atoms such as cyclohexane or "petroleum ether" of boiling point in the range 40°–180° C., preferably 60°–80° C., 80°–100° C. or 100°–120° C. or a liquid aromatic hydrocarbon, e.g. of 6–9 carbon atoms such as benzene, toluene or xylene; the solvent is one which dissolves the acid ester and organotin ester. However, preferably an inert water immiscible liquid solvent, in particular one capable of forming an azeotrope with water, is absent so the reaction is preferably carried out in the absence of any organic solvent, though the organotin halide and carboxyl compound may be dispersed in water. The ratio of the number of equivalents of base e.g. hydroxide to total moles of water added is usually 0.001–0.5:1 such as 0.01–0.2:1, e.g. 0.03:1 to 0.08:1. Preferably the reaction is carried out in the substantial absence of any added compound of formula $R^2YH$ e.g. an alcohol, e.g. with less than 10 mole% based on the number of g. atoms of halogen in the organotin halide.

The addition of base to acid ester and organotin halide and the reaction are carried out under conditions of time, temperature and proportions of the three reactants that there is little or no hydrolysis of the organotin product. Increased hydrolysis with any particular acid ester results from increasing the time of addition or reaction, increasing the temperature of the addition or reaction, increasing the proportion of base to acid ester or organotin chloride. Reducing the alkyl chain length of the alkyl group of an alkyl acid ester or replacing it by a benzyl group also increases the likelihood of hydrolysis as does increasing the basic strength of the base and/or increasing the concentration of base in the second mixture, and/or increasing the atomic weight of the halogen and/or increasing the first acid dissociation constant of the acid $R_3(COOH)_{m+n}$ (i.e. decreasing the $pK_a$).

The reaction is usually carried out at below the boiling point of the mixture but while reaction temperatures of $-30°$ C. to the boiling point may be used, temperatures of 10° C. to the boiling point, e.g. 20°–70° are often desirable in order to speed the desired reaction but not too high as to cause significant hydrolysis of the ester. Total addition and reaction time of 1 minute to 24 hours e.g. 5 mins. to 2 hrs. are often suitable. The total reaction is usually carried out for a time and at a temperature, such that not more than 10% of the acid ester is hydrolysed. The base often in aqueous solution is preferably added at 20°–70° C. to an agitated mixture of carboxyl compound, organotin halide and water at 20°–70° C. over 1 sec. to 3 hrs. with a further optional treatment of the reaction mixture for up to 5 hrs., e.g. 0.5–2 hrs. further at 20°–70° C. The pH of the reaction mixture after the addition but before the further heating (if any) is preferably 1.5–7, e.g. 2–4.5 such as 3–4.

With dialkyltin dichlorides and alkyl maleate half esters total reaction times of 5 mins. to 5 hrs., at 20°–70° C., e.g. 30 mins. to 2 hrs. at 20°–70° C. have been found suitable.

The addition and reaction are preferably carried out under conditions such that the organotin product at the end of the reaction contains a weight ratio of chlorine to tin of less than 1:8, e.g. 1:600 to 1:8, preferably 1:600 to 1:15, and especially 1:600 to 1:32, such as 1:600 to 1:100 and corresponding weight ratios of the same atom ratio as above when the halogen is bromine or iodine. These conditions especially apply to reaction of dialkyltin dichlorides, such as dibutyl dichloride, and monoalkyl maleates, with 3–12 carbon atoms, particularly 6–10 carbon atoms in the alkyl group in the ester, the organotin product at the end of the reaction preferably containing less than 2% Cl, e.g. less than 1.2% Cl, preferably less than 0.5% Cl; chlorine contents of 0.05–0.15% with dibutyl bis (octyl maleate) isomers are highly advantageous.

At the end of the reaction there are produced 2 liquid layers, one comprising the organotin ester product and the other an aqueous layer; the organotin ester layer is separated from the aqueous layer. In addition or alternatively, in order to improve the separation between the layers, the reaction liquid may be extracted with an inert water immiscible liquid solvent such as a hydrocarbon such as paraffin or petroleum ether or aromatic hydrocarbon such as benzene, toluene or xylene, or a chlorinated hydrocarbon or an ether. The extract may be separated and the organotin product recovered by evaporation. If a water immiscible solvent has been used in the reaction, then at the end the organic extract layer is separated from the aqueous layer.

Preferably as soon as possible after the reaction is complete, the 2 layers are separated, and advantageously the layer containing the organotin ester is washed with water, before being dried e.g. under vacuum.

When a in the organotin compound is 1, the organotin compound is a mono organotin tris ester, i.e. a stannoic acid ortho ester (or thio ester); when a is 2, it is a diorganotin bis ester (or thio ester). Preferably, a is 2, and the process is particularly directed to preparing diorganotin esters of half esters of dicarboxylic acids, e.g. di butyltin bis (methyl maleate) or bis (isooctyl maleate).

In a particularly preferred process, the aqueous solution of base, which is an alkali metal hydroxide, is added to an agitated mixture of water, a carboxyl compound of formula ($R^2$OOC) $R^3$ COOH) where $R^2$ and $R^3$ are as defined above, but preferably $R^2$ is an alkyl group of 1-18 carbon atoms and $R^3$ is a group of formula cis —CH=CH—, and a diorganotin chloride of formula $R_2'$SnCl$_2$ where R' is defined above but is preferably an alkyl group of 1-10 carbon atoms, in a molar ratio of 1.9:1 to 2.2:1 (e.g. about 2:1) preferably at 20°–70° C., the number of equivalents to the hydroxide being between 101–120%, e.g. 102–116% especially 104–112% of the number of g. atoms of chlorine in the organotin, to form an organotin ester, e.g. of formula $R_2'$Sn (OOC $R^3$COOR$^2$)$_2$ substantially free of organotin compounds containing Sn-Cl bonds (e.g. less than 1.5% Cl particularly less than 1.2% Cl), the addition and reaction being carried out at less than the boiling point of the reaction mixture, e.g. at 20°–70° C. to produce 2 liquid layers, an organotin layer and an aqueous layer.

The organotin esters (and thio esters) prepared by the process of this invention may be used as heat stabilizers for halogen containing polymers; the esters (and thio esters) may be added to the polymers in amounts of 0.1–10% by weight of polymer. The organotin esters may be used as sole stabilizers or may be mixed with other organotin compounds or extended with the unreacted acid ester or alkyl alkanoates with 1-8 carbons in the alkyl group and 6–20 carbons in the alkanoate. The polymers may be homopolymers or copolymers of vinyl chloride or vinylidene chloride, or copolymers or either or both of these with other olefinic copolymerizable monomers, e.g. vinyl acetate. The polymers contain at least 40% by weight of chlorine.

The invention is illustrated in the following Examples.

In the following Examples 1–15, an aqueous solution of a base is added at the temperature specified to a stirred mixture of di-n-butyl tin dichloride (DBTC), mono isoctyl maleate (IOM) and water at the specified temperature, before extra heating if any, stirring was stopped and the mixture allowed to cool. Two liquid phases were formed, one primarily containing the organotins and the other an aqueous phase. The phase were separated and the organotin layer, optionally after washing with water, dried, weighed and analysed for Sn, Cl. The results are given in the attached Table. In the Table the asterisk denotes a process in which the organotin layer was washed. The product is crude dibutyltin bis (isooctyl maleate). In Example 14, the base was added as a solid, the extra water having been added previously.

| Example | DBTC g | 10 M g | Water g | Added Together Base Nature | Base g | Molar % Base to DBTC % | Water g | Addition time & temp. °C | Further reaction Time & Temp. °C | pH after Addition | Product g | Product yield % | Product % Sn | Yield on Sn % | Product % Cl |
|---|---|---|---|---|---|---|---|---|---|---|---|---|---|---|---|
| 1 | 76 | 114 | 95.5 | NaOH | 19.3 | 193 | 58 | 10 min 55°–60° | 2 hr 55°–60° | 2 | 162.5 | 94.6 | 18.0 | 98.4 | 1.1 |
| 2 | 76 | 114 | 100 | NaOH | 20.8 | 208 | 60 | 30 min 60° | 1 hr 55°–60° | 3 | 164.0 | 95.5 | 18.0 | 99.3 | 0.6 |
| 3 | 76 | 114 | 100 | NaOH | 21.2 | 212 | 62 | 30 min 50°–55° | 1 hr 50° | | 164.2 | 95.6 | 18.2 | 100.6 | 0.5 |
| 4 | 76 | 114 | 100 | NaOH | 22.0 | 220 | 62 | 20 min 50°–60° | 1 hr 50°–60° | | 160.2* | 93.1 | 17.8 | 95.9 | 0.05 |
| 5 | 76 | 114 | 100 | NaOH | 22.4 | 224 | 62 | 20 min 50°–60° | 1 hr 50°–60° | 7 | 160.1* | 93.1 | 18.05 | 97.1 | 0.05 |
| 6 | 66.7 | 100 | 88 | NaOH | 19.3 | 213.3 | 55 | 60 min 50°–60° | — | | 143.9 | 96.1 | 17.9 | 99.5 | 0.23 |
| 7 | 66.7 | 100 | 88 | NaOH | 18.4 | 203.2 | 55 | 60 min 55°–60° | 1 hr 55°–60° | | 144.8 | 96.7 | 17.7 | 99.5 | 0.91 |
| 8 | 66.7 | 100 | 88 | NaOH | 20.2 | 223 | 55 | 60 min 55°–60° | 1 hr 55°–60° | | 143.0 | 95.5 | 17.9 | 99.0 | 0.15 |
| 9 | 66.7 | 100 | 88 | NaOH | 21.0 | 232 | 55 | 60 min 55°–60° | 1 hr 55°–60° | | 146.5 | | 17.4 | 98.5 | — |
| 10 | 66.7 | 100 | 88 | NaOH | 19.3 | 216 | 55 | 60 min 30° | 1 hr 30° | | 144.1 | 96.2 | 17.9 | 99.3 | 0.18 |
| 11 | 66.7 | 100 | 88 | Na$_2$CO$_3$ | 23.3 | 100 | 55 | 20 min 45° | 1 hr 45° | 3 | 143.7 | 95.4 | | | 0.7% |
| 12 | 66.7 | 100 | 88 | aq. NH$_3$ | (26.8 ml 34.8% w/w) | 220 | 47.5 extra | 30 min 35° | None | | 147.1 | 97.6 | | | 0.82 |
| 13 | 66.7 | 100 | 88 | aq. NH$_3$ | 29.7 ml 34.8% w/w | 240 | 47.5 extra | 1 hr at 45° | None | 4 | 146.0 | 96.9 | 17.56 | 98.2 | 0.2 |
| 14 | 66.7 | 100 | 88 | NaHCO$_3$ solid | 39.9 | 216 | 55 | 20 min 45° | 1 hr 45° | | 144.6 | 96.0 | | | 0.11 |
| 15 | 66.7 | 100 | 88 | Na$_2$CO$_3$ | 25.1 | 216 | 55 | 20 min 45° | 1 hr 45° | 3–4 | 146.0 | 96.9 | | | 0.16 |

EXAMPLES 16-17

The effectiveness of organotin compounds prepared in previous Examples as heat stabilizers for polyvinyl chloride was compared to that of dibutyltin (bis isoctyl maleate), prepared commercially from dibutyl tin oxide and iso octyl maleate. In each case the following mixture was made; Polyvinyl chloride powder (sold under the Trade Name Corvic 50/16) (100 parts), an acrylic polymer processing aid (sold under the Trade Name Paraloid K120M) (1 part), lubricant mixture of cetyl and stearyl alcohols (sold under the Trade Name Laurex CS) (1 part) and organotin stabilizer (1 part). The mixture was heated on milling rolls at 146° C. until homogenous, then samples taken and press and oven aged at 190° C. for 5, 10, 15, 20 and 30 mins. The colours of the aged samples were compared. The results were as follows:

| Example | Stabilizer from Example Number | % Cl in Stabilizer | Functional performance compared to Standard |
|---|---|---|---|
| 16 | 8 | 0.15 | Equal |
| 17 | 7 | 0.91 | Equal up to 25 mins, slight decrease thereafter |

EXAMPLES 18-22

In a similar manner to the process of Example 8, dibutyl tin bis (alkyl maleates) were made from alkyl maleates other than the iso octyl maleate. The results were as follows:

| Example | 18/19 | 20 | 21 | 22 |
|---|---|---|---|---|
| Nature of alkyl group in alkyl maleate | isopropyl | Butyl | cyclohexyl | 2-Ethyl hexyl |
| Addition Temperature °C. | 40 | 40 | 50 | 50 | 50 |
| Addition Time | 1hr | 1hr | 1hr | 1hr | ½hr |
| Further Reaction Time | 1hr | 1hr | 1hr | 1hr | 1hr |
| Further Reaction Temp °C. | 40 | 40 | 50 | 50 | 50 |
| Molar percent NaOH to DBTC | 204 | 216 | 216 | 216 | 216 |
| Yield Weight % | 81 | 80 | 89 | 90 | 92 |
| Yield on Sn % | 94.7 | | 94.0 | 94.2 | 94.9 |
| % Cl | 1.6 | 1.3 | 0.62 | 0.44 | 0.12 |

We claim:

1. A process for preparing organotin esters of a carboxylic acid which comprises adding a base to an agitated mixture of (i) an organotin chloride of formula $R'_2SnCl_2$ wherein each of $R'$ is an organic group, and (ii) a carboxyl compound, which is a maleate half ester of formula $R^2OOC-CH=CH-COOH$ wherein $R^2$ is an alkyl group of 3-20 carbon atoms or a cyclohexyl group, the addition being carried out in the presence of added water, and producing a second mixture which is reacted to form an organotin product comprising an organotin ester with at least one maleate group attached to a tin atom, said product containing tin and chlorine with a weight ratio of chlorine to tin of less than 1:8, the amount of organotin chloride, carboxyl compound and base being such that for each mole of organotin chloride, there are 1.95-2.4 moles carboxyl compound and 1.9-2.5 equivalents of base, the proportion of the number of equivalents of base to equivalents of carboxyl compound being 0.9-1.3:1 and the proportion of equivalents of base to moles of added water being 0.001-0.5:1.

2. A process according to claim 1 wherein the base is an aqueous solution of an alkali metal hydroxide.

3. A process according to claim 1 wherein the amount of base is such as to provide 1.02-1.25 equivalents per g atom of chlorine in the organotin chloride.

4. A process according to claim 3 wherein the base provides 1.04-1.12 equivalents per g atom of chlorine.

5. A process according to claim 1 wherein $R'$ is butyl.

6. A process according to claim 1 wherein $R'$ is an alkyl group which contains 1-8 carbon atoms.

7. A process according to claim 1 wherein $R'$ is octyl.

8. A process according to claim 1 wherein $R'$ is phenyl.

9. A process according to claim 1 wherein $R^2$ is an alkyl group of 4-10 carbon atoms or a cyclohexyl group.

10. A process according to claim 1 wherein the maleate half ester is a mono octyl maleate isomer.

11. A process according to claim 1, 2 or 3 wherein the reaction is carried out at less than the boiling point of the mixture to produce 2 liquid layers, an organotin layer and an aqueous layer.

12. A process according to claim 1, 2 or 3 wherein the reaction is carried out at 20°-70° C.

13. A process according to claim 6 wherein an aqueous solution of an alkali metal hydroxide is added to an agitated mixture of an organotin halide of formula $R'_2SnCl_2$ and a maleate half ester of formula $R^2OOC CH=CHCOOH$ wherein $R^2$ is an alkyl group of 4 to 10 carbon atoms.

14. A process according to claim 6 or 10 wherein the reaction is carried out at less than the boiling point of the mixture to produce 2 liquid layers, an organotin layer and an aqueous layer.

15. A process according to claim 1 wherein an aqueous solution of the base which is an alkali metal hydroxide is added to an agitated mixture of water, a carboxyl compound, and the diorganotin dichloride, wherein $R'$ is an alkyl group of 4-10 carbon atoms, in a molar ratio of carboxyl compound to diorganotin dichloride of 1.9:1 to 2.2:1, the number of equivalents of hydroxide being between 104-112% of the number of g. atoms of chlorine, to form an organotin ester of formula $R_2'Sn(OOC CH=CH COOR^2)_2$ containing chlorine and tin, in a weight ratio of 1:600 to 1:15 and the reaction is carried out at less than the boiling point of the mixture to produce 2 liquid layers, an organotin layer and an aqueous layer.

* * * * *

UNITED STATES PATENT AND TRADEMARK OFFICE
CERTIFICATE OF CORRECTION

PATENT NO. : 4,231,949

DATED : November 4, 1980

INVENTOR(S) : MARIO Q. CEPRINI et al

It is certified that error appears in the above-identified patent and that said Letters Patent are hereby corrected as shown below:

Title page, first column, after "Assignee": replace "Albright & Wilson Limited, Warley, England" with ---Tenneco Chemicals Inc., Saddle Brook, New Jersey---.

Column 10, line 44, after "claim 1" insert -- or 10 --.

Signed and Sealed this

Thirty-first Day of March 1981

[SEAL]

Attest:

RENE D. TEGTMEYER

Attesting Officer     Acting Commissioner of Patents and Trademarks